| United States Patent [19] | [11] | 4,342,870 |
|---|---|---|
| Kennis et al. | [45] | Aug. 3, 1982 |

[54] NOVEL 3-(1-PIPERIDINYLALKYL)-4H-PYRIDO[1,2-A]PYRIMIDIN-4-ONE DERIVATIVES

[75] Inventors: Ludo E. J. Kennis, Turnhout; Josephus C. Mertens, Oud-Turnhout, both of Belgium

[73] Assignee: Janssen Pharmaceutica N.V., Beerse, Belgium

[21] Appl. No.: 191,632

[22] Filed: Sep. 29, 1980

Related U.S. Application Data

[63] Continuation-in-part of Ser. No. 134,845, Mar. 28, 1980, abandoned.

[51] Int. Cl.³ .......................................... C07D 401/12
[52] U.S. Cl. ..................................................... 544/282
[58] Field of Search .......................................... 544/282

[56] References Cited

U.S. PATENT DOCUMENTS 3,412,094 11/1968 Rorig et al. .......................... 544/282

FOREIGN PATENT DOCUMENTS 52-5795 1/1977 Japan .................................... 544/282

Primary Examiner—Donald G. Daus
Assistant Examiner—Sharon A. Gibson
Attorney, Agent, or Firm—Geoffrey G. Dellenbaugh

[57] ABSTRACT

Novel 3-(1-piperidinylalkyl)-4H-pyrido[1,2-a]pyrimidin-4-one derivatives, wherein the piperidine ring is substituted with an aroyl radical or a functional derivative thereof, said compounds being potent serotonin-antagonists.

6 Claims, No Drawings

NOVEL 3-(1-PIPERIDINYLALKYL)-4H-PYRIDO[1,2-A]PYRIMIDIN-4-ONE DERIVATIVES

CROSS-REFERENCE TO RELATED APPLICATIONS

This is a continuation-in-part of our copending application Ser. No. 134,845, filed Mar. 28, 1980, now abandoned.

BACKGROUND OF THE INVENTION

In Japanese Kokai Number 7 6146-497 and in Ann. Rep. Sankyo Res. Lab. 29, 75-98 (1977) there are described a number of 4H-pyrido[1,2-a]pyrimidin-4-one derivatives, bearing in the 3-position an aminoalkyl substituent, wherein the amino group may be part of a morpholino-, a piperidino- or a piperazine moiety. Said compounds are tought to be useful as cardiovascular agents and to act on the central nervous system.

The compounds of the present invention differ from the prior art compounds by the presence of particular substituents on the piperidine ring and by their pharmacological activities.

DESCRIPTION OF THE PREFERRED EMBODIMENTS

This invention is concerned with a novel series of 3-[(1-piperidinyl)alkyl]-4H-pyrido[1,2-a]pyrimidin-4-one derivatives which are structurally represented by the formula

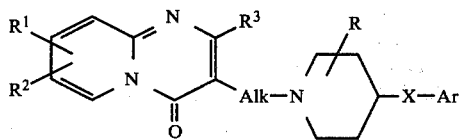
(I)

and the pharmaceutically acceptable acid addition salts thereof, wherein $R^1$ and $R^2$ are each independently selected from the group consisting of hydrogen, lower alkyl, lower alkyloxy, halo and trifluoromethyl;
$R^3$ is a member selected from the group consisting of hydrogen, lower alkyl and aryl;
Alk is a lower alkylene radical;
R is a member selected from the group consisting of hydrogen, lower alkyl, hydroxy, lower alkyloxy and hydroxymethyl in the 2-, 3- or 4-position of the piperidine ring;
X is a member selected from the group consisting of $>C=O$, $>CHOH$,

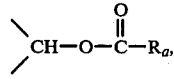

$>CH_2$, $>C(O\text{-lower alkyl})_2$,

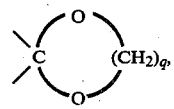

$>C=NOH$ and $>C=N-NH_2$, wherein said $R_a$ is hydrogen or lower alkyl and said q is the integer 2 or 3; and
Ar is aryl; wherein said aryl is a member selected from the group consisting of phenyl, substituted phenyl, thienyl, furanyl and pyridinyl, wherein said substituted phenyl has from 1 to 3 substituents each independently selected from the group consisting of halo, lower alkyl, lower alkyloxy, trifluoromethyl, nitro, amino and hydroxy.

As used in the foregoing definitions the term "halo" in generic to fluoro, chloro, bromo and iodo; "lower alkyl" is meant to include straight and branched saturated hydrocarbon radicals, having from 1 to 6 carbon atoms such as, for example, methyl, ethyl, 1-methylethyl, 1,1-dimethylethyl, propyl, butyl, pentyl, hexyl and the like; and "lower alkylene", as used in the definition of Alk, comprises straight and branched saturated alkylene chains having from 1 to 4 carbon atoms.

Preferred compounds within the scope of formula (I) are those wherein R is hydrogen. Particularly preferred compounds are those wherein R is hydrogen and X is $>C=O$, $>C(O\text{-lower alkyl})_2$ or

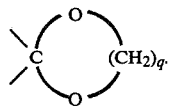

Especially preferred compounds are those wherein R is hydrogen, X is C=O and Alk is an 1,2-ethanediyl radical. The compound 3-[2-[4-(4-fluorobenzoyl)-1-piperidinyl]ethyl]-2-methyl-4H-pyrido[1,2-]pyrimidin-4-one is the most preferred.

The compounds of formula (I) have basic properties and, consequently, they may be converted to their therapeutically active non-toxic acid addition salt forms by treatment with appropriate acids, such as, for example, inorganic acids, such as hydrohalic acid, e.g., hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, benzoic, 3-phenyl-2-propenoic, α-hydroxybenzeneacetic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) can generally be prepared by the reaction of an appropriate reactive ester of formula (II) with an appropriately substituted piperidine of formula (III). In the reactive ester (II) $R^1$, $R^2$, $R^3$ and Alk are as previously described and W represents a reactive ester group such as, for example, halo, particularly chloro, bromo or iodo, or a sulfonyloxy group, e.g., methylsulfonyloxy, 4-methylphenylsulfonyloxy and the like. In the piperidine (III), R, X and Ar are as previously described.

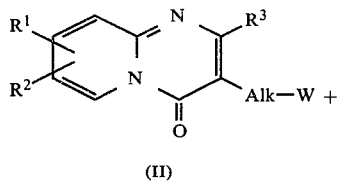

(II)

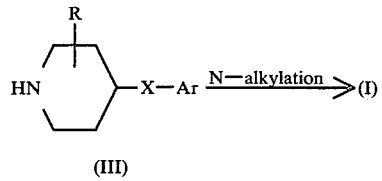

(III)

The foregoing reaction may be carried out following standard N-alkylating procedures. Said reaction is preferably carried out in an appropriate reaction-inert organic solvent such as, for example, a lower alkanol, e.g., methanol, ethanol, propanol, butanol and the like alkanols; an aromatic hydrocarbon, e.g., benzene, methylbenzene, dimethylbenzene, and the like; an ether, e.g., 1,4-dioxane, 1,1'-oxybispropane and the like; a ketone, e.g., 4-methyl-2-pentanone, N,N-dimethylformamide; nitrobenzene; and the like. The addition of an appropriate base such as, for example, an alkali or earth alkaline metal carbonate or hydrogen carbonate, may be utilized to pick up the acid which is liberated during the course of the reaction. A small amount of an appropriate metal iodide, e.g., sodium or potassium iodide may be added as a reaction promotor. Somewhat elevated temperatures are appropriate to enhance the rate of the reaction and preferably the reaction is carried out at the reflux temperature of the reaction mixture.

The compounds of formula (I) may also be prepared following art-known cyclization procedures for preparing 4H-pyrido[1,2-a]pyrimidin-4-ones, as described, for example, in Ann. Rep. Sankyo Res. Lab. 29, 75-98 (1977).

For example, the compounds of formula (I) may be prepared by cyclizing an appropriately substituted 2-aminopyridine (IV) with an appropriate cyclizing agent of formula (V) following art-known procedures of preparing 4H-pyrido[1,2-a]pyrimidin-4-ones as described, for example, in J. Heterocyclic Chem. 16, 137-144 (1979). $R^1$, $R^2$, $R^3$, Alk, X, R and Ar in the reagents (IV) and (V) are as previously described, while L represents an appropriate leaving group such as, for example, lower alkyloxy, hydroxy, halo, amino, mono- and di(-lower alkyl)amino and the like.

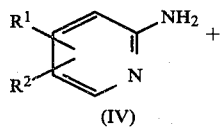

(IV)

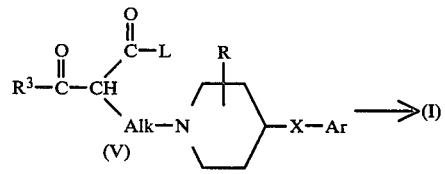

(V)

The above cyclization-reaction may be carried out by stirring the reagents together, if desired, in the presence of a suitable reaction inert solvent such as, for example, an aliphatic-, alicyclic- or aromatic hydrocarbon, e.g, hexane, cyclohexane, benzene and the like; pyridine; N,N-dimethylformamide and the like amides. Elevated temperatures may be appropriate to enhance the reaction-rate. Sometimes it may be preferable to carry out the reaction at the reflux temperature of the reaction mixture.

The compounds of formula (I) may also be derived from a compound of formula (VI) wherein P represents a precursor of the corresponding Ar-X-radical by converting said P-radical into the desired Ar-X-radical following methods known in the art.

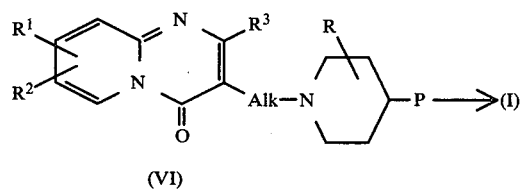

(VI)

For example, the compounds of formula (I) wherein Ar-X- is an optionally substituted 2-aminobenzoyl radical, said compounds being represented by the formula (I-a), may be prepared by the oxidative cleavage of the double bond in the corresponding 3-indoyl-derivative (VII) and subsequent hydrolysis of the thus formed formamide (VIII). Said oxidative cleavage may be carried out, for example, by the reaction of (VII) with an appropriate oxidizing agent, such as, for example, sodium periodate in the presence of a catalytic amount of osmium tetroxide in a suitable solvent, e.g., 1,4-dioxane and the like. The oxidation may equally well be carried out by bubbling ozonized oxygen through a solution of (VII) in acetic acid and subsequently decomposing the intermediately formed ozonide with water. The thus obtained (formylamino)phenylcarbonyl intermediate (VIII) is then converted into (I-a) by hydrolysis in acidic medium. In the following reaction-scheme $R^1$, $R^2$, $R^3$, Alk and R are as previously defined and $R^4$ and $R^5$ are each independently selected from the group consisting of hydrogen, halo, lower alkyl, lower alkyloxy, trifluoromethyl, nitro, amino and hydroxy.

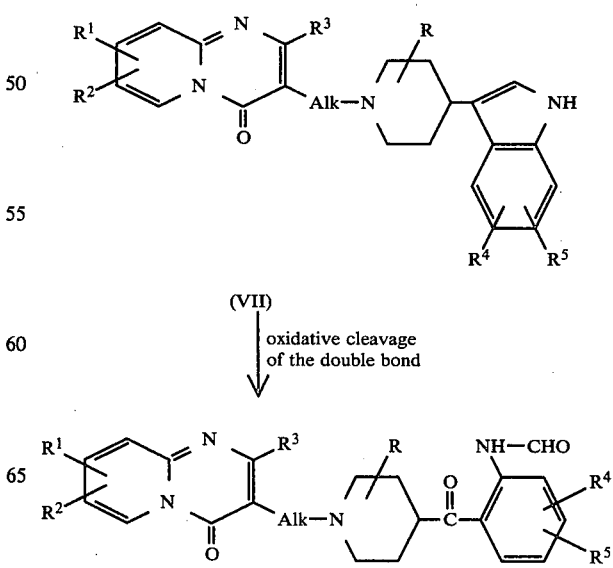

(VIII)

↓ hydrolysis

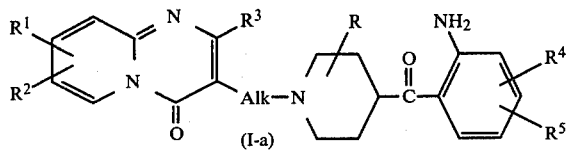
(I-a)

The intermediates of formula (VII) as well as the pharmaceutically acceptable acid addition salts thereof, constitute a useful intermediates and as potent serotonin antagonists an additional feature of the present invention.

The compounds of formula (I) wherein X is a CHOH-radical (I-b), may generally be derived from the corresponding aroyl compounds, (I-c), by reducing the carbonyl group of the latter with an appropriate reducing agent, e.g., sodium borohydride, sodium cyano borohydride and the like following art-known methodologies.

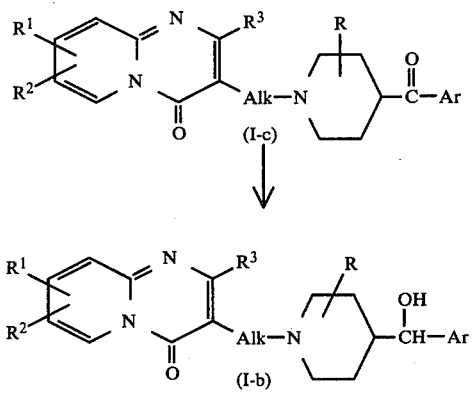

When, for example, sodium borohydride is used as a reducing agent the reaction may conveniently be carried out in alkaline aqueous medium, if desired, in admixture with a water-miscible organic solvent such as, for example, an alicyclic ether, e.g., tetrahydrofuran, 1,4-dioxane and the like; or a lower alkanol, e.g., methanol, propanol and the like.

The compounds of formula (I) wherein X represents a radical $>CH-O-C(O)-R_a$, wherein $R_a$ has the previously defined meaning, (I-d), may be derived from the corresponding alcohols (I-b) by acylating the latter with an appropriate acylating agent according to art-known procedures. Appropriate acylating agents which may be used for this purpose include lower alkanoic acids and acyl halides and anhydrides derived therefrom.

(I-b) $\xrightarrow{\text{acylation}}$

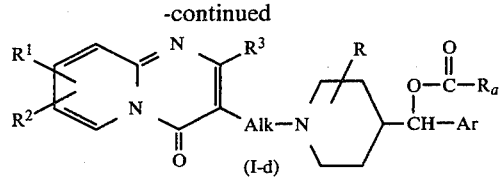
(I-d)

The compounds of formula (I) wherein X is a methylene radical, (I-e), may be derived from the corresponding carbonyl derivatives, (I-c), by the reduction of said carbonyl group to a methylene group, e.g., by the Clemmensen reduction, using amalgated zinc and hydrochloric acid, or by the Wolff-Kishner reduction, using hydrazine and alkali in a high-boiling polar solvent, such as, 1,2-ethanediol and the like.

(I-c) $\xrightarrow{\text{reduction}}$

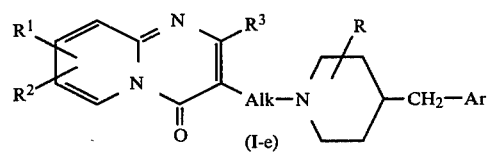
(I-e)

The compounds of formula (I) wherein X is $>C(O-$lower alkyl$)_2$ or

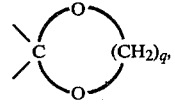

wherein said q is as previously described, may be derived from the corresponding carbonyl compounds by subjecting the latter to a ketalization-reaction following methodologies generally known in the art. Cyclic lower alkylene ketals, for example, may be prepared following methodologies analogous to those described in Synthesis, 1974, (1) 23-26.

The compounds of formula (I) wherein X represents a radical of the formual $>C=NOH$ or a radical of the formula $>C=N-NH_2$ can easily be derived from the corresponding carbonyl compounds by reacting the latter with respectively hydroxylamine hydrochloride or hydrazine hydrochloride according to art-known procedures of preparing oximes and hydrazones.

The compounds of formula (I) wherein R represents a hydroxymethyl radical in the 4-position of the piperidine ring, (I-f), may be prepared by reacting a compound of formula (I) wherein R is hydrogen, (I-g) with formaldehyde or a polymer thereof, paraformaldehyde.

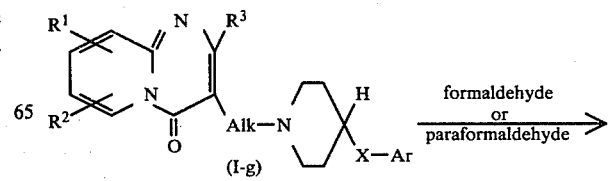
(I-g) $\xrightarrow{\text{formaldehyde or paraformaldehyde}}$

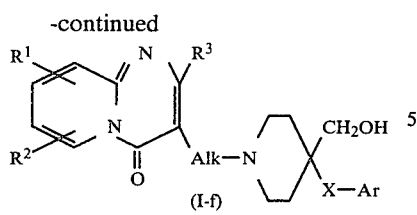

(I-f)

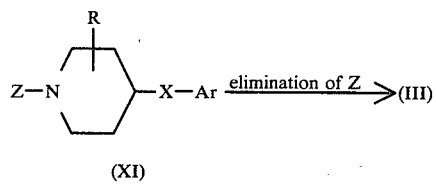

(XI)

The hydroxymethylation reaction is preferably carried out by stirring and, if desired, heating the starting compound (I-g) in a suitable polar solvent, such as, for example, pyridine, methanol and the like, preferably in the presence of an appropriate base. Suitable bases are, for example, methanaminium hydroxides, e.g. N,N,N-trimethylbenzenemethanaminium hydroxide and the like.

Certain of the intermediates and starting materials used in the foregoing preparations are known compounds, others may be prepared according to art-known methodologies of preparing similar compounds and some of them are novel and consequently their preparation will be described hereafter.

The intermediates of formula (II) can be prepared by converting the hydroxyl function of the corresponding alcohols (IX) into a reactive leaving group, e.g., by reacting the alcohols (IX) with thionyl chloride, sulfuryl chloride, phosphor pentabromide, phosphoryl chloride, methanesulfonyl chloride, 4-methylbenzenesulfonyl chloride and the like.

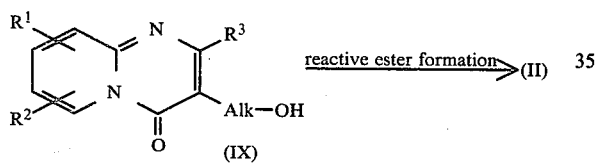

The alcohols (IX), used as starting materials herein, may be prepared by cyclizing an appropriately substituted 2-aminopyridine (IV) with a reagent having the formula

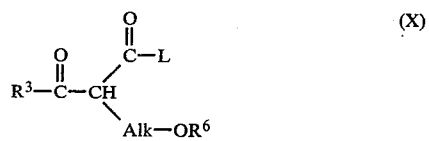

wherein $R^3$, Alk and L are as previously described and $R^6$ is hydrogen, or, $R^6$ and L, when taken together, form a direct bond. This cyclization reaction may be carried out following the same procedure as previously described for the preparation of (I) starting from (IV) and (V).

The intermediates of formula (III) may be derived from an intermediate of formula (XI) by eliminating the protective group Z following art-known procedures, depending upon the nature of Z. For example, in case Z is a phenylmethyl radical, said elimination may be carried out by a catalytic hydrogenolysis reaction in the presence of an appropriate catalyst, e.g., palladium-on-charcoal and the like or in case Z is a lower alkyloxycarbonyl radical, the elimination may be carried out by hydrolysis in acidic medium.

In case Z represents a phenylmethyl radical it may be advantageous to convert previously said phenylmethyl group into a lower alkyloxycarbonyl group following art-known procedures and subsequently eliminating said lower alkyloxycarbonyl group as described hereinabove.

The piperidines (XI), used as starting materials herein, may be prepared following art-known procedures, depending upon the nature of X.

For example, the intermediates of formula (XI) wherein X is CO, (XI-a), may be prepared starting from an appropriately substituted 4-piperidinone (XII) and an appropriate arylacetonitrile (XIII) as shown in the following reaction-scheme.

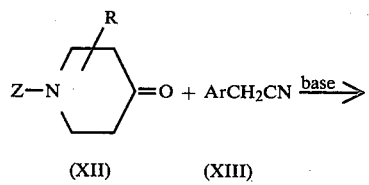

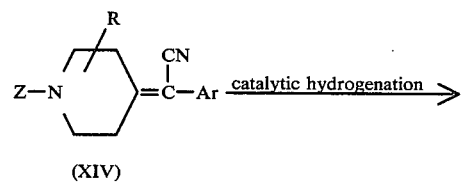

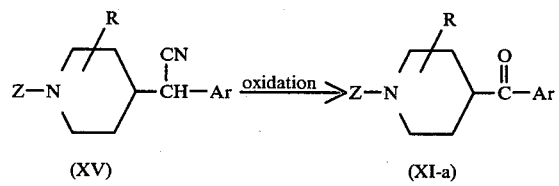

The reaction of (XII) with (XIII) can be carried out by stirring and, if desired, heating the reactants together in a suitable reaction-inert solvent in the presence of a suitable base, e.g., sodium methanolate and the like bases. The catalytic hydrogenation of (XIV), yielding the nitrile (XV), may be carried out in a suitable reaction-inert solvent, e.g., methanol and the like, in the presence of an appropriate catalyst, e.g., palladium-on-charcoal, and, if desired, in the presence of a catalyst-poison, e.g., thiophene and the like. The oxidation of (XV) may be carried out following art-known oxidative procedures as described, for example, in Journal of Organic Chemistry 40, 267 (1975).

The intermediates of formula (XI-a) wherein R is other than hydroxy, said R being represented by R' and said intermediates by the formula (XI-a-1), may also be prepared by the reaction of an appropriately substituted 4-piperidinyl magnesium halide (XVI) with an appropriate nitrile (XVII), following art-known Grignard-reaction procedures.

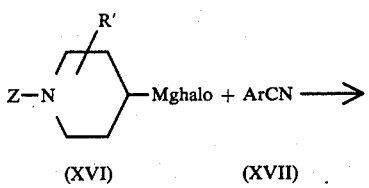

(XVI)   (XVII)

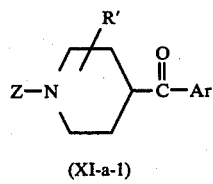

(XI-a-1)

The intermediates of formula (III) wherein X is other than CO, (III-b), can be derived from the corresponding arylcarbonylpiperidines, (III-a), following the same procedures as described hereinbefore for the preparations of the compounds (I-b), (I-d) and (I-e) starting from (I-c).

The intermediates of formula (III) wherein R represents a hydroxymethyl radical in the 4-position of the piperidine ring, (III-d), can be derived from the corresponding piperidines wherein R is hydrogen, (III-c), following the same procedure as described hereinbefore for the preparation of (I-f) starting from (I-g).

The intermediates of formula (V) can generally be prepared by reacting an appropriate keto-ester or keto-amide (XVIII) with an appropriately substituted piperidine (XIX) following art-known alkylating procedures. The piperidine (XIX) may be prepared by N-alkylating an appropriately substituted piperidine (XX) with an appropriate reagent (XXI), wherein W' has the same meaning as W, provided that W' has a better leaving capacity than W.

W—Alk—W' + HN⟨piperidine-R⟩—X—Ar  →^{N-alkylation}

(XXI)   (XX)

W—Alk—N⟨piperidine-R⟩—X—Ar (XIX)

(XIX) + R³—C(O)—CH₂—C(O)—L  →^{C-alkylation} (V)

(XVIII)

The intermediates of formula (VI) can be prepared by reacting an appropriate reactive ester (II) with an appropriately substituted piperidine (XXII) following the same procedure as previously described for the preparation of (I) starting from (II) and (III).

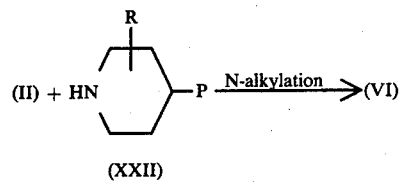

(XXII)

The intermediates of formula (VII) may be prepared by N-alkylating a piperidine (XXIII) with an appropriate reactive ester of formula (II) following standard N-alkylating procedures.

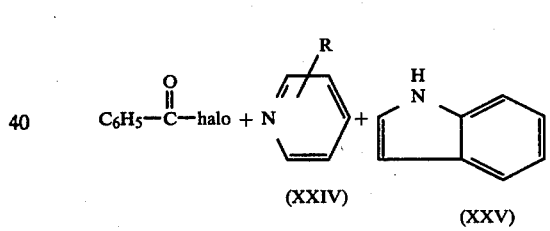

(XXIII)

The piperidines (XXIII), used as starting materials herein, are described in Belg. Pat. No. 858,101 and can be prepared by condensating benzoyl halide with an appropriately substituted pyridine (XXIV) and an appropriately substituted 1H-indole (XXV), subsequently reducing the thus obtained dihydropyridine (XXVI), e.g., by catalytically hydrogenating the latter in the presence of an appropriate catalyst such as, for example, palladium-on-charcoal and the like, and hydrolyzing the benzoyl derivative (XXVII) in alkaline medium.

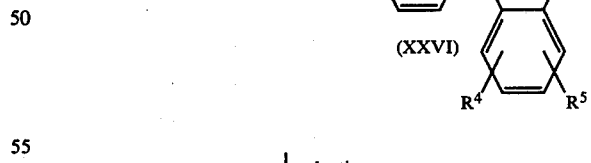

(XXIV)   (XXV)

condensation reaction →

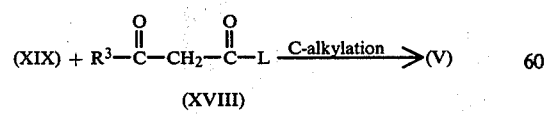

(XXVI)

↓ reduction

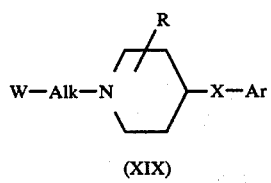

-continued
(XXVII)

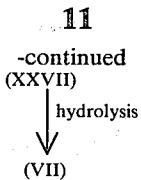

↓ hydrolysis (VII)

The compounds of formula (I), the intermediates of formula (VII) and the pharmaceutically acceptable acid addition salts thereof have useful pharmacological properties. They are very potent serotoninantagonists and as such they can be used in the treatment of a variety of diseases in which serotonin release is of predominant importance. The potency of the subject compounds as serotonin-antagonists is clearly evidenced by the results obtained in the following tests wherein the antagonistic activity of the compounds (I) and the intermediates (VII) on the effect of serotonin is examined.

Test 1: Antagonistic activity on the effect of serotonin on the caudal artery of the rat.

Caudal arteries from fasted male rats (210–235 g) are used in the test. Two helical strips having a length of 5–6 cm and a width of 2 mm are obtained from each artery and mounted vertically in a 100 ml organ bath containing an oxygenated Krebs-Henseleit solution. Submaximal contractions of the arterial strips are produced by adding single doses of serotonin (40 ng/ml) to the organ bath for 2 minutes with each time an interval of 10 minutes. The amplitude of the contraction is measured before and 5 minutes after adding the drug. After washing out, the agonist is added again three times in order to see whether the contraction is restored and normalized. The first column of tables 1 and 2 shows the $ED_{50}$-values in ng/ml for a number of compounds of formula (I) and the intermediates (VII) in the above test. In this connection the $ED_{50}$-values are the minimal concentrations of the concerned drugs which reduce the amplitude of the contraction to at least 50% of its normal value.

Test 2: Effects in gastric lesion tests a. Lesions induced by compound 48/80

Compound 48/80 (a mixture of oligomers obtained by condensation of 4-methoxy-N-methylbenzeneethanamine and formaldehyde) is a potent releaser of vasoactive amines from endogenous stores such as, for example, histamine and serotonin. Rats injected with compound 48/80 exhibit consistent changes of blood flow in different vascular beds: cyanosis of the ears and the extremities are prominent within five minutes after injection of the compound; the rats die from shock within 30 minutes. The shock, followed by dead, can be avoided if the rats are pretreated with a classical H 1 antagonist. However the stimulatory effects on gastric secretion are not suppressed so that rats treated with compound 48/80 and protected from shock by an H 1 antagonist may exhibit all signs of intensive gastric gland activity: gross autopsy shows distended stomachs with abnormal contents and rough bright red patches all over the mucosa, corresponding to areas of disintegrated glands. A number of known serotonin antagonists such as, for example, methysergide, cyproheptadine, cinanserin, mianserin, pipamperone, spiperone, pizotifen and metergoline, prevent completely the cyanosis of ears and extremities as well as the lesions in the glandular area of the stomach and the abnormal gastric distension.

b. Method

Male rats of a Wistar inbred strain, weighing 200–250 g, are starved overnight, water being available ad libitum. The test compounds are administered orally as a solution or as a suspension in aqueous medium. A control rat and a "blank" rat receive the test compound. One hour later 5-[4-(diphenylmethyl)-1-piperazinylmethyl]-1-methyl-1H-benzimidazole-2-methanol is administered subcutaneously to all rats at the dose of 2.5 mg/kg. Two hours after the oral administration of the test compound, the compound 48/80 (freshly solved in water at a concentration of 0.25 mg/ml) is injected intravenously into all rats (dose: 1 mg/kg) except the "blank" rats. Four hours after the intravenous injection of compound 48/80, the rats are decapitated and the stomachs are removed. Subsequently the stomachs are inspected for distension and contents (blood, fluid, food) and thoroughly rinsed. The macroscopic lesions are secured from 0 to +++, 0 corresponding to complete absence of visible lesions and the highest score corresponding to reddish rough patches covering more than half the glandular area. The second column of tables 1 and 2 shows for a number of compounds of formula (I) and the intermediates (VII) the doses (in mg/kg body weight) at which the distension of the stomach as well as the lesions in the glandular area of the stomach are completely absent in 50% of the test rats ($ED_{50}$-values).

The compounds listed in tables 1 and 2 are not given for the purpose of limiting the invention thereto but only to exemplify the useful pharmacological activities of all the compounds within the scope of formula (I) and of all the intermediates within the scope of formula (VII).

TABLE 1

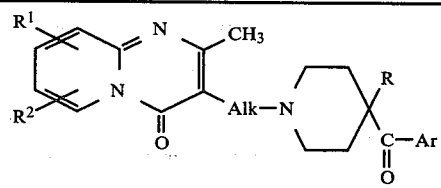

| $R^1$ | $R^2$ | Alk | R | Ar | Caudal Artery $ED_{50}$ in ng/ml | Gastric lesion $ED_{50}$ in mg/kg |
|---|---|---|---|---|---|---|
| H | H | —CH$_2$—CH$_2$— | H | C$_6$H$_4$.4F | 0.32 | 0.016 |
| H | 6-CH$_3$ | —CH$_2$—CH$_2$— | H | C$_6$H$_4$.4F | <0.63 | 2.5 |
| H | H | —CH$_2$—CH$_2$— | OH | C$_6$H$_4$.4F | 0.31 | 2.5 |
| H | H | —CH$_2$—CH$_2$— | H | C$_6$H$_5$ | 0.63 | 0.63 |
| H | H | —CH$_2$—CH$_2$— | H | 2-thienyl | 1.3 | — |
| H | H | —CH$_2$—CH$_2$— | CH$_3$ | C$_6$H$_4$.4F | 0.63 | 0.16 |

TABLE 1-continued

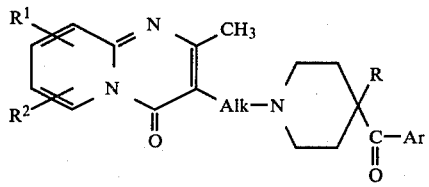

| $R^1$ | $R^2$ | Alk | R | Ar | Caudal Artery $ED_{50}$ in ng/ml | Gastric lesion $ED_{50}$ in mg/kg |
|---|---|---|---|---|---|---|
| H | H | $-CH_2-CH_2-$ | H | $C_6H_4.2CH_3$ | 1.25 | — |
| H | 8-$CH_3$ | $-CH_2-CH_2-$ | H | $C_6H_4.4F$ | <2.5 | 0.04 |
| H | 7-Cl | $-CH_2-CH_2-$ | H | $C_6H_4.4F$ | 1.25 | 0.01 |
| H | 7-$CH_3$ | $-CH_2-CH_2-$ | H | $C_6H_4.4F$ | 0.31 | 0.02 |
| 6-$CH_3$ | 8-$CH_3$ | $-CH_2-CH_2-$ | H | $C_6H_4.4F$ | 0.16 | 0.02 |
| H | H | $-CH_2-CH-$<br>$\quad\quad\;\;\;\|$<br>$\quad\quad\;\;CH_3$ | H | $C_6H_4.4F$ | — | 2.5 |
| H | 7-Br | $-CH_2-CH_2-$ | H | $C_6H_4.4F$ | 0.31 | <0.63 |
| H | H | $-CH_2-CH_2-$ | $-CH_2OH$ | $C_6H_4.4F$ | — | <0.63 |

TABLE 2

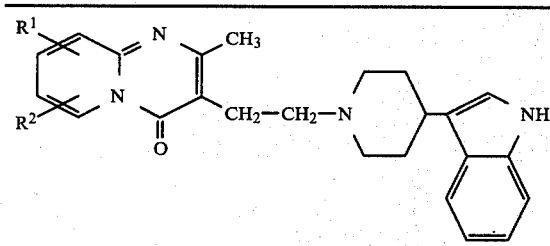

| $R^1$ | $R^2$ | Caudal Artery $ED_{50}$ in ng/ml | Gastric lesion $ED_{50}$ in mg/kg |
|---|---|---|---|
| H | H | 0.14 | 0.08 |
| H | 8-$CH_3$ | 0.31 | 0.04 |
| H | 7-$CH_3$ | 0.31 | 0.63 |
| H | 7-Cl | 0.63 | 0.63 |
| 6-$CH_3$ | 8-$CH_3$ | 0.16 | 0.63 |
| H | 7-Br | 0.31 | 1.25 |
| H | 6-$CH_3$ | 0.08 | 0.16 |

The compounds of formula (I) and the intermediates of formula (VII) prevent completely the lesions which are caused by excessive serotonin release and they also block the serotonin-induced contractions of bronchial tissues and of blood vessels, arteries as well as veins, and, consequently, the compounds of the present invention can be used in the treatment of gastrointestinal ulcus, bronchial spasm, hemorrhoids, varises and the like diseases, all of which are caused by congestion.

In view of their useful anti-congestive properties, the subject compounds may be formulated into various pharmaceutical forms for administration purposes. To prepare the pharmaceutical compositions of this invention, an effective anti-congestive amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Acid addition salts of (I) and (VII), due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Although the amount of the active ingredient to be administered may vary within rather wide limits depending on the particular circumstances, such as the nature and the severity of the disease, doses of from about 0.005 to about 1 mg of active ingredient per kg of body weight, and particularly from about 0.01 to about 0.5 mg per kg of body weight, administered once or repeatedly, are in general satisfactory.

The following formulations exemplify typical anticonvulsant pharmaceutical compositions in dosage unit form suitable for systemic administration to animal and human subjects in accordance with the present invention. These examples are given to illustrate and not to limit the scope of the present invention.

Oral drops

The following formulation provides 50 liters of an oral-drop solution comprising 10 mg of 3-[2-[4-(4-fluorobenzoyl)-1-piperidinyl]-ethyl]-2-methyl-4H-pyrido[1,2-a]pyrimidin-4-one as the active ingredient (A.I.) per milliliter.

| A.I. | 500 grams |
|---|---|
| 2-hydroxypropanoic acid | 0.5 liters |
| sodium saccharin | 1750 grams |
| cocoa flavor | 2.5 liters |
| purified water | 2.5 liters |
| polyethylene glycol q.s. ad | 50 liters |

The A.I. is dissolved in the 2-hydroxypropanoic acid and 1.5 liters of the polyethylene glycol at 60°–80° C. After cooling to 30°–40° C. there are added 35 liters of polyethylene glycol and the mixture is stirred well. Then there is added a solution of the sodium saccharin in 2.5 liters of purified water and while stirring there are added the cocoa flavor and polyethylene glycol q.s. ad volume. The resulting solution is filled into suitable containers.

Oral solution

The following formulation provides 20 liters of an oral solution comprising 20 mg of 3-[2-[4-(4-fluorobenzoyl)-1-piperidinyl]ethyl]-2-methyl-4H-pyrido[1,2-a]pyrimidin-4-one as the active ingredient (A.I.) per teaspoonful (5 milliliters).

| A.I. | 20 grams |
|---|---|
| 2,3-dihydroxybutanedioic acid | 10 grams |
| sodium saccharin | 40 grams |
| 1,2,3-propanetriol | 12 liters |
| Sorbitol 70% solution | 3 liters |
| Methyl 4-hydroxybenzoate | 9 grams |
| Propyl 4-hydroxybenzoate | 1 gram |
| Raspberry essence | 2 milliliters |
| Gooseberry essence | 2 milliliters |
| Purified water q.s. ad 20 liters. | |

The methyl and propyl 4-hydroxybenzoates are dissolved in 4 liters of boiling purified water. In 3 liters of this solution are dissolved first the 2,3-dihydroxybutanedioic acid and thereafter the A.I. The latter solution is combined with the remaining part of the former solution and the 1,2,3-propanetriol and the sorbitol solution are added thereto. The sodium saccharin is dissolved in 0.5 liters of water and the raspberry and gooseberry essences are added. The latter solution is combined with the former, water is added q.s. ad volume and the resulting solution is filled in suitable containers.

Capsules

The following formulation provides 1000 capsules comprising each 20 mg of 3-[2-[4-(4-fluorobenzoyl)-1-piperidinyl]ethyl]-2,4-methyl-4H-pyrido[1,2-a]pyrimidin-4-one as the active ingredient (A.I.).

| A.I. | 20 grams |
|---|---|
| Sodium lauryl sulfate | 6 grams |

-continued

| Starch | 56 grams |
|---|---|
| Lactose | 56 grams |
| Colloidal silicon dioxide | 0.8 grams |
| Magnesium strearate | 1.2 grams |

The composition is prepared by stirring the ingredients vigorously together. The resulting mixture is subsequently filled into suitable hardened gelatine capsules.

Film-coated tablets 10,000 compressed tablets, each containing as the active ingredient 10 mg of 3-[2-[4-(4-fluorobenzoyl)-1-piperidinyl]ethyl]-2-methyl-4H-pyrido[1,2-a]pyrimdin-4-one, are prepared from the following formulation:

| Tablet core: | | |
|---|---|---|
| | A.I. | 100 grams |
| | Lactose | 570 grams |
| | Starch | 200 grams |
| | Polyvinylpyrrolidone (Kollidon-K 90) | 10 grams |
| | Microcrystalline cellulose (Avicel) | 100 grams |
| | Sodium dodecyl sulfate | 5 grams |
| | Hydrogenated vegetable oil (Sterotex) | 15 grams |
| Coating: | | |
| | Methyl cellulose (Methocel 60 HG) | 10 grams |
| | Ethyl cellulose (Ethocel 22 cps) | 5 grams |
| | 1,2,3-propanetriol | 2.5 milliliters |
| | Polyethylene glycol 6000 | 10 grams |
| | Concentrated colour suspension (Opaspray K-1-2109) | 30 milliliters |
| | Polyvinylpyrrolidone (Povidone) | 5 grams |
| | Magnesium octadecanoate | 2.5 grams |

Preparation of tablet core

A mixture of the A.I., the lactose and the starch is mixed well and thereafter humidified with a solution of the sodium dodecyl sulfate and the polyvinylpyrrolidone in about 200 milliliters of water. The wet powder mixture is sieved, dried and sieved again. Then there is added the microcrystalline cellulose and the hydrogenated vegetable oil. The whole is mixed well and compressed into tablets.

Coating

To a solution of the methyl cellulose in 75 milliliters of denaturated ethanol there is added a solution of the ethyl cellulose in 150 milliliters of dichloromethane. Then there are added 75 milliliters of dichloromethane and the 1,2,3-propanetriol. The polyethylene glycol is molten and dissolved in 75 milliliters of dichloromethane. The latter solution is added to the former and then there are added the magnesium octadecanoate, the polyvinylpyrrolidone and the concentrated colour suspension and the whole is homogenated.

The tablet cores are coated with the thus obtained mixture in a coating apparatus.

Injectable solution

The following formulation provides 1 liter of a parenteral solution comprising 4 mg of 3-[2-[4-(4-fluorobenzoyl)-1-piperidinyl]-ethyl]-2-methyl-4H-pyrido[1,2-a]pyrimidin-4-one as the active ingredient milliliter.

| A.I. | 4 grams |
| --- | --- |
| Lactic acid | 4 grams |
| Propylene glycol | 0.05 grams |
| Methyl 4-hydroxybenezoate | 1.8 grams |
| Propyl 4-hydroxybenzoate | 0.2 grams |
| Purified water q.s. ad 1 liter. | |

The methyl and propyl 4-hydroxybenzoates are dissolved in about 0.5 liters of boiling water for injection. After cooling to about 50° C. there are added while stirring the lactic acid, the propylene glycol and the A.I. The solution is cooled to room temperature and supplemented with water for injection q.s. ad volume. The solution is sterilized by filtration (U.S.P. XVII p. 811) and filled in sterile containers.

Suppositories

100 Suppositories each containing 20 mg of 3-[2-[4-(4-fluorobenzoyl)-1-piperidinyl]ethyl]-2-methyl-4H-pyrido[1,2-a]pyrimidin-4-one as the active ingredient are prepared from the following formulations:

| A.I. | 3 grams |
| --- | --- |
| 2,3-Dihydroxybutanedioic acid | 3 grams |
| Polyethylene glycol 400 | 25 milliliters |
| Surfactant (Span) | 12 grams |
| Triglycerides (Witepsol 555) q.s. ad | 300 grams. |

The A.I. is dissolved in a solution of the 2,3-dihydroxybutanedioic acid in the polyethylene glycol 400. The surfactant and the triglycerides are molten together. The latter mixture is mixed well with the former solution. The thus obtained mixture is poured into moulds at a temperature of 37°–38° C. to form the suppositories.

In view of the anti-congestive activity of the subject compounds, it is evident that the present invention provides a method of treating congestive diseases of warm-blooded animals by the systemic administration of an effective anti-congestive amount of a compound of formula (I) or of an intermediate of formula (VII) or a pharmaceutically acceptable acid addition salt thereof in admixture with a pharmaceutical carrier.

The following examples are intended to illustrate but not to limit the scope of the present invention. Unless otherwise stated all parts herein are by weight and all temperatures are in the centigrade scale.

A. Preparation of intermediates

Example I

To a stirred mixture of 80 parts of sodium methoxide and 160 parts of methanol are added successively 50 parts of 2-thiopheneacetonitrile and then dropwise 66 parts of 1-(phenylmethyl)-4-piperidinone. Upon completion, the whole is heated to reflux and stirring at reflux temperature is continued for one hour. The reaction mixture is cooled and evaporated. The residue is distilled in a molecular distillation-apparatus, yielding about 70 parts of α-[1-(phenylmethyl)-4-piperidinylidene]-2-thiopheneacetonitrile as a residue.

In a similar manner there is also prepared: 4-methyl-α-[1-(phenylmethyl)-4-piperidinylidene]benzeneacetonitrile; mp. 193.4° C.

Example II

A mixture of 70 parts of α-[1-(phenylmethyl)-4-piperidinylidene]-2-thiopheneacetonitrile in 800 parts of methanol is hydrogenated at normal pressure and at room temperature with 10 parts of palladiumon charcoal catalyst 10%. After the calculated amount of hydrogen is taken up, the catalyst is filtered off and the filtrate is evaporated, yielding 70 parts of 1-(phenylmethyl)-α-(2-thienyl)-4-piperidineacetonitrile as a residue.

In a similar manner there is also prepared: dl-α-(4-methylphenyl)-4-piperidineacetonitrile as a residue.

Example III

To a mixture of 74 parts of dl-α-(4-methylphenyl)-4-piperidineacetonitrile, 95.4 parts of sodium carbonate, a few crystals of potassium iodide in 1840 parts of 4-methyl-2-pentanone are added portionwise 39.21 parts of (chloromethyl)benzene. After the addition is complete, the whole is stirred and refluxed for 24 hours. The reaction mixture is cooled and 400 parts of water are added. The organic layer is separated, dried over potassium carbonate, filtered and evaporated. The oily residue is dissolved in 1,1'-oxybisethane and gazeous hydrogen chloride is introduced to the solution. The precipitated hydrochloride salt is filtered off and dried, yielding 68 parts of dl-α-(4-methylphenyl)-1-(phenylmethyl)-4-piperidineacetonitrile monohydrochloride; mp. 212°–213° C.

Example IV

To a stirred mixture of 29.6 parts of 1-(phenylmethyl)-α-(2-thienyl)-4-piperidineacetonitrile in 100 parts of dimethyl sulfoxide are added portionwise 4 parts of a sodium hydride dispersion 60%. Upon completion, stirring is continued overnight. The reaction mixture is poured onto water. The precipitated product is filtered off and extracted with trichloromethane. The extract is dried, filtered and evaporated. The residue is crystallized from 2,2'-oxybispropane, yielding 10 parts (35%) of [1-(phenylmethyl)-4-piperidinyl](2-thienyl)methanone; mp. 100.5° C.

In a similar manner there is also prepared: (4-methylphenyl)[1-(phenylmethyl)-4-piperidinyl]methanone; mp. 83.9° C.

Example V

To 5 parts of magnesium are added 2.18 parts of 1,2-dibromoethane and a small amount of iodine to initiate the reaction. Then there is added dropwise a solution of 28 parts of 4-chloro-1-methylpiperidine in 180 parts of tetrahydrofuran while the mixture is heated to 70° C. After cooling, there is added dropwise a solution of 14 parts of 3-methylbenzonitrile in 90 parts of tetrahydrofuran. Upon completion, stirring is continued for 1 hour at reflux temperature. The reaction mixture is cooled and poured onto a solution of 75 parts of ammonium chloride in water. The product is extracted with 2,2'-oxybispropane. The extract is washed with water, dried, filtered and evaporated, yielding 35 parts of (3-methylphenyl) (1-methyl-4-piperidinyl)methanone as an oily residue.

Example VI

To 7 parts of magnesium is added dropwise a solution of 50 parts of 1-bromo-2-methylbenzene in 140 parts of 1,1'-oxybisethane so that the mixture is refluxing. The whole is stirred for 15 minutes at reflux. The Grignard-complex is cooled to 10° C. and there is added dropwise a solution of 30 parts of 1-(phenylmethyl)-4-piperidinecarbonitrile in 70 parts of 1,1'-oxybisethane. Upon completion, stirring is continued for 4 hours at room temperature. The reaction mixture is decomposed with a solution of 40 parts of ammonium chloride in 400 parts of water. The organic phase is separated, dried, filtered and evaporated, yielding 31 parts of (2-methylphenyl) [1-(phenylmethyl)-4-piperidinyl]methanone as an oily residue.

In a similar manner there is also prepared: (4-fluorophenyl) [4-methyl-1-(phenylmethyl)-4-piperidinyl]methanone as an oily residue.

EXAMPLE VII

To a stirred and cooled (10°–15° C.) Grignard-complex, previously prepared starting from 13.5 parts of 4-chloro-1-methylpiperidine and 2.4 parts of magnesium in 68 parts of tetrahydrofuran, is added dropwise a solution of 10 parts of 4-bromobenzonitrile in 22 parts of tetrahydrofuran. Upon completion, stirring is continued for 1 hour at reflux temperature. The reaction mixture is decomposed by pouring onto a mixture of 50 parts of ammonium chloride in 250 parts of water. The product is extracted with methylbenzene. The extract is dried, filtered and evaporated. The residue is purified by column-chromatography over silica gel using a mixture of trichloromethane and methanol (95:5 by volume) as eluent. The pure fractions are collected and the eluent is evaporated, yielding 10 parts of (4-bromophenyl)-(1-methyl-4-piperidinyl)methanone as a residue.

Example VIII

A mixture of 12 parts of ethyl carbonochloridate, 31 parts of (2-methylphenyl)[1-(phenylmethyl)-4-piperidinyl]methanone and 270 parts of dimethylbenzene is stirred and refluxed for 4 hours. The reaction mixture is evaporated and the residue is dissolved in trichloromethane. The solution is washed with a dilute hydrochloric acid solution. The organic phase is separated, dried, filtered and evaporated, yielding 20 parts of ethyl 4-(2-methylbenzoyl)-1-piperidinecarboxylate as an oily residue.

Example IX

Following the procedure described in Example VIII and using equivalent amounts of the appropriate starting materials there are also prepared:
ethyl 4-(2-thienylcarbonyl)-1-piperidinecarboxylate as a residue;
ethyl 4-(4-methylbenzoyl)-1-piperidinecarboxylate as a residue; and
ethyl 4-(4-fluorobenzoyl)-4-methyl-1-piperidinecarboxylate as a residue.

Example X

To a stirred mixture of 35 parts of (3-methylphenyl) (1-methyl-4-piperidinyl)methanone, 1 part of sodium carbonate and 225 parts of dimethylbenzene are added dropwise 22 parts of ethyl carbonochloridate at 20° C. Upon completion, stirring is continued for 6 hours at reflux temperature. The reaction mixture is evaporated, yielding 12 parts of ethyl 4-(3-methylbenzoyl)-1-piperidinecarboxylate as an oily residue.

In a similar manner there is also prepared: ethyl 4-(4-bromobenzoyl)-1-piperidinecarboxylate as a residue.

Example XI

A mixture of 103 parts of ethyl 4-(4-methylbenzoyl)-1-piperidinecarboxylate and 900 parts of a hydrobromic acid solution 48% in water is stirred and refluxed for 3 hours. The reaction mixture is stirred and allowed to cool in an ice-bath. The precipitated product is filtered off, washed with water and stirred in 2-propanone, yielding 91 parts (86%) of (4-methylphenyl)(4-piperidinyl)methanone hydrobromide; mp. +300° C.

Example XII

Following the same hydrolysis-procedure as described in Example XI there are also prepared:
(3-methylphenyl)(4-piperidinyl)methanone hydrobromide;
(4-bromophenyl)(4-piperidinyl)methanone hydrobromide;
(2-methylphenyl)(4-piperidinyl)methanone hydrobromide;
(4-piperidinyl)(2-thienyl)methanone hydrobromide; and
(4-fluorophenyl)(4-methyl-4-piperidinyl)methanone hydrobromide.

Example XIII

A mixture of 3.8 parts of 3-(2-chloroethyl)-2,8-dimethyl-4H-pyrido[1,2-a]pyrimidin-4-one, 3 parts of 3-(4-piperidinyl)-1H-indole, 10 parts of sodium carbonate, 0.1 parts of potassium iodide and 240 parts of 4-methyl-2-pentanone is stirred and refluxed for 20 hours. The reaction mixture is filtered hot over Hyflo and the filtrate is evaporated. The residue is purified by column-chromatography over silica gel using a mixture of trichloromethane and methanol (90:10 by volume) as eluent. The pure fractions are collected and the eluent is evaporated. The residue is crystallized from a mixture of 2-propanol, 2,2'-oxybispropane and 4-methyl-2-pentanone, yielding 4.7 parts of 3-[2-[4-(1H-indol-3-yl)-1-piperidinyl]ethyl]-2,8-dimethyl-4H-pyrido[1,2-a]pyrimidin-4-one; mp. 235.9° C.

Example XIV

Following the procedure described in Example XIII and using equivalent amounts of the appropriate starting materials there are also prepared:
3-[2-[4-(1H-indol-3-yl)-1-piperidinyl]ethyl]-2,7-dimethyl-4H-pyrido-[1,2-a]pyrimidin-4-one; mp. 203.7° C.;
7-chloro-3-[2-[4-(1H-indol-3-yl)-1-piperidinyl]ethyl]-2-methyl-4H-pyrido[1,2-a]pyrimidin-4-one; mp. 240.9° C.;
3-[2-[4-(1H-indol-3-yl)-1-piperidinyl]ethyl]-2,6,8-trimethyl-4H-pyrido[1,2-a]pyrimidin-4-one; mp. 223.4° C.; and
7-bromo-3-[2-[4-(1H-indol-3-yl)-1-piperidinyl]ethyl]-2-methyl-4H-pyrido[1,2-a]pyrimidin-4-one; mp. 224.8° C.

Example XV

A mixture of 4.8 parts of 3-(2-chloroethyl)-2,6-dimethyl-4H-pyrido[1,2-a]pyrimidin-4-one, 4 parts of 3-(4-piperidinyl)-1H-indole, 8.5 parts of sodium carbonate and 120 parts of 4-methyl-2-pentanone is stirred and refluxed overnight using a water-separator. The reaction mixture is cooled, water is added and the precipitated product is filtered off. It is dissolved in a mixture of trichloromethane and methanol (90:10 by volume). The solution is filtered over silica gel and the filtrate is evaporated. The residue is crystallized from 2-propanol, yielding 2.5 parts (31%) of 3-[2-[4-(1H-indol-3-yl)-1-piperidinyl]ethyl]-2,6-dimethyl-4H-pyrido[1,2-a]pyrimidin-4-one; mp. 224.9° C.

Example XVI

Following the procedure described in Example XV and using equivalent amounts of the appropriate starting materials there is also prepared:

3-[2-[4-(1H-indol-3-yl)-1-piperidinyl]ethyl]-2-methyl-4H-pyrido[1,2-a]pyrimidin-4-one; mp. 209.2° C.

Example XVII

A mixture of 155 parts of 1-fluoro-3-methoxybenzene, 75 parts of aluminium chloride and 650 parts of 1,2-dichloroethane is stirred and 113 parts of 1-acetyl-4-piperidinecarbonyl chloride are added portionwise. Upon completion, stirring is continued for 1 hour at 40°-50° C. The reaction mixture is poured onto a mixture of crushed ice and hydrochloric acid. The product is extracted with methylbenzene. The extract is dried, filtered and evaporated. The residue is purified by high pressure liquid-chromatography over silica gel using a mixture of trichloromethane, hexane and methanol (47.5:47.5:5 by volume) as eluent. The first fraction (A-isomer) is collected and the eluent is evaporated, yielding 1-acetyl-4-(2-fluoro-4-methoxybenzoyl)-piperidine. The second fraction (B-isomer) is collected and the eluent is evaporated, yielding 40 parts (25%) of 1-acetyl-4-(4-fluoro-2-hydroxybenzoyl)piperidine.

A mixture of 40 parts of 1-acetyl-4-(4-fluoro-2-hydroxybenzoyl)piperidine and 150 parts of a hydrochloric acid solution 6N is stirred and refluxed for 3 hours. The reaction mixture is cooled. The precipitated product is filtered off, washed with 2-propanone and dried, yielding 29 parts (87%) of (4-fluoro-2-hydroxyphenyl)(4-piperidinyl)methanone hydrochloride; mp. +300° C.

Example XVIII

To a stirred mixture of 4 parts of a sodium hydride dispersion 60% in 180 parts of methylbenzene are added dropwise 12 parts of ethyl 3-oxobutanoate at room temperature. Then there is added 1 part of N,N,N-tridecylmethanammonium chloride and the whole is warmed to 40° C. At this temperature, a solution of 25 parts of [1-(3-chloropropyl)-4-piperidinyl](4-fluorophenyl)methanone in 45 parts of methylbenzene is added slowly. The whole is heated to reflux and stirring is continued overnight at reflux temperature. The reaction mixture is cooled to room temperature and filtered over Hyflo. The filtrate is evaporated, yielding 24 parts of ethyl α-acetyl-4-(4-fluorobenzoyl)-1-piperidinepentanoate as a residue.

B. Preparation of the final compounds

Example XIX

A mixture of 5 parts of 3-(2-chloroethyl)-2-methyl-4H-pyrido-[1,2-a]pyrimidin-4-one, 4.9 parts of (4-fluorophenyl)(4-piperidinyl)-methanone hydrochloride, 5 parts of sodium carbonate and 160 parts of 4-methyl-2-pentanone is stirred and refluxed for 24 hours. The reaction mixture is cooled, washed with water and the layers are separated. The organic phase is dried, filtered and evaporated. The residue is purified by column-chromatography over silica gel using a mixture of trichloromethane and methanol (92:8 by volume) as eluent. The pure fractions are collected and the eluent is evaporated. The residue is crystallized from a mixture of ethanol and 1,1'-oxybisethane, yielding 3 parts of 3-[2-[4-(4-fluorobenzoyl)-1-piperidinyl]ethyl]-2-methyl-4H-pyrido[1,2-a]pyrimidin-4-one; mp. 139° C.

Example XX

Following the procedure described in Example XIX and using equivalent amounts of the appropriate starting materials there are also prepared:

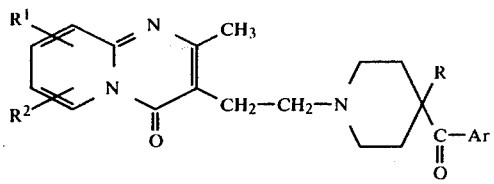

| R¹ | R² | R | Ar | base or salt form | mp. °C. |
|---|---|---|---|---|---|
| H | H | H | C₆H₄.4CH₃ | base | 139.3 |
| H | H | H | C₆H₄.4OCH₃ | base | 153.6 |
| H | H | H | C₆H₄.3CF₃ | base | 137.6 |
| H | H | H | C₆H₄.2OH | base | 155.3 |
| H | 6-CH₃ | H | C₆H₄.4F | base | 138.9 |
| H | H | OH | C₆H₄.4F | ½iC₃H₇OH.H₂O | 161.5 |

Example XXI

A mixture of 5.6 parts of 3-(2-chloroethyl)-2-methyl-4H-pyrido[1,2-a]pyrimidin-4-one, 6 parts of phenyl(4-piperidinyl)-methanone hydrobromide, 8 parts of sodium carbonate, 0.1 parts of potassium iodide and 240 parts of 4-methyl-2-pentanone is stirred and refluxed for 24 hours using a water-separator. The reaction mixture is filtered hot over Hyflo and the filtrate is evaporated. The residue is purified by column-chromatography over silica gel using a mixture of trichloromethane and methanol (90:10 by volume) as eluent. The pure fractions are collected and the eluent is evaporated. The residue is crystallized from a mixture of ethanol and 1,1'-oxybisethane, yielding 6 parts of 3-[2-(4-benzoyl-1-piperidinyl)ethyl]-2-methyl-4H-pyrido[1,2-a]pyrimidin-4-one; mp. 122.2° C.

Example XXII

Following the procedure described in Example XXI and using equivalent amounts of the appropriate starting materials there are also prepared:

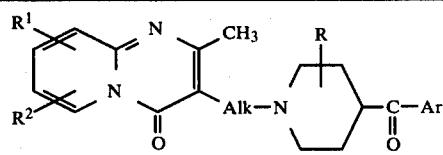

| R¹ | R² | Alk | R | Ar | base or salt form | mp °C. |
|---|---|---|---|---|---|---|
| H | H | —CH₂—CH₂— | H | 2-thienyl | base | 144.1 |
| H | H | —CH₂—CH₂— | H | C₆H₄.3CH₃ | base | 123.5 |
| H | H | —CH₂—CH₂— | H | C₆H₄.3CH₃ | 2HCl.H₂O | +300 |

-continued

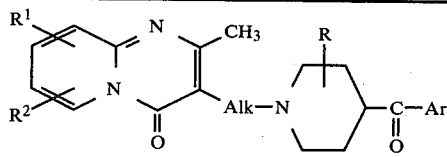

| R¹ | R² | Alk | R | Ar | base or salt form | mp °C. |
|---|---|---|---|---|---|---|
| H | H | —CH₂—CH₂— | 4-CH₃ | C₆H₄.4F | base | 109.6 |
| H | H | —CH₂—CH₂— | 4-CH₃ | C₆H₄.4F | 2HCl.H₂O | 262.5 |
| H | H | —CH₂—CH₂— | H | C₆H₄.2CH₃ | base | 115.5 |
| H | H | —CH₂—CH₂— | H | C₆H₄.4Br | base | 157.8 |
| H | 8-CH₃ | —CH₂—CH₂— | H | C₆H₄.4F | base | 169.2 |
| H | 7-Cl | —CH₂—CH₂— | H | C₆H₄.4F | base | 194.1 |
| H | 7-CH₃ | —CH₂—CH₂— | H | C₆H₄.4F | base | 167 |
| H | H | —CH₂—CH₂— | H | C₆H₄.3F | base | 136.2 |
| 6-CH₃ | 8-CH₃ | —CH₂—CH₂— | H | C₆H₄.4F | base | 136.3 |
| H | H | —CH₂—CH—<br>       \|<br>       CH₃ | H | C₆H₄.4F | base | 157.5 |
| H | 7-Br | —CH₂—CH₂— | H | C₆H₄.4F | base | 208.3 |
| H | H | —CH₂—CH₂— | H | C₆H₃.2OH, 4F | 2 HCl | +300 |

Example XXIII

A mixture of 7.9 parts of 3-[2-[4-(4-fluorobenzoyl)-1-piperidinyl]ethyl]-2-methyl-4H-pyrido[1,2-a]pyrimidin-4-one, 3 parts of paraformaldehyde, 2 parts of N,N,N,-trimethylbenzenemethanaminium hydroxide solution 40% in methanol and 100 parts of pyridine is stirred over week-end at 60°–70° C. The reaction mixture is evaporated and the residue is stirred in water. The product is extracted with trichloromethane. The extract is dried, filtered and evaporated. The residue is purified by column-chromatography over silica gel using a mixture of trichloromethane and methanol (95:5 by volume) as eluent. The pure fractions are collected and the eluent is evaporated. The residue is converted into the hydrochloride salt in 2-propanol. The salt is filtered off and crystallized from ethanol, yielding 1.7 parts (16.5%) of 3-[2-[4-(4-fluorobenzoyl)-4-(hydroxymethyl)-1-piperidinyl]ethyl]-2-methyl-4H-pyrido[1,2-a]pyrimidin-4-one dihydrochloride monohydrate; mp. 215.5° C.

Example XXIV

A solution of 2 parts of 3-[2-[4-(4-fluorobenzoyl)-1-piperidinyl]ethyl]-2-methyl-4H-pyrido[1,2-a]pyrimidin-4-one in 64 parts of 2-propanol is warm acidified with 2-propanol saturated with hydrogen chloride. The formed hydrochloride salt is allowed to crystallize. It is filtered off and dried, yielding 2 parts (85.5%) of 3-[2-[4-(4-fluorobenzoyl)-1-piperidinyl]ethyl]-2-methyl-4H-pyrido[1,2-a]pyrimidin-4-one dihydrochloride; mp. +300° C.

In a similar manner there are also prepared: 3-[2-[4-(4-fluorobenzoyl)-1-piperidinyl]ethyl]-2-methyl-4H-pyrido-[1,2-a]pyrimidin-4-one sulfate (1:2); mp. 254.7° C.; and 3-[2-[4-(4-fluorobenzoyl)-1-piperdinyl]ethyl]-2-methyl-4H-pyrido-[1,2-a]pyrimidin-4-one phosphate (1:2); mp. 243.8° C.

Example XXV

To a stirred solution of 2 parts of 3-[2-[4-(4-fluorobenzoyl)-1-piperidinyl]ethyl]-2-methyl-4H-pyrido[1,2-a]pyrimidin-4-one in 32 parts of 2-propanol is added a solution of 0.59 parts of (Z)-2-butenedioic acid in 16 parts of 2-propanol. The product is allowed to crystallize. It is filtered off and dried, yielding 2.1 parts (82%) of 3-[2-[4-(4-fluorobenzoyl)-1-piperidinyl]ethyl]-2-methyl-4H-pyrido[1,2-a]pyrimidin-4-one (Z)-2-butenedioate (1:1); mp. 180.2° C.

In a similar manner there is also prepared: (+)-3-[2-[4-(4-fluorobenzoyl)-1-piperidinyl]ethyl]-2-methyl-4H-pyrido[1,2-a]pyrimidin-4-one [R-(R*,R*)]-2,3-dihydroxybutanedioate (1:1); mp. 155.3° C.

Example XXVI

A mixture of 24 parts of ethyl α-acetyl-4-(4-fluorobenzoyl)-1-piperidinepentanoate, 30 parts of 2-pyridinamine and 6 parts of polyphosphoric acid is stirred and heated to 160° C.: a violent reaction occurs (temperature rises to 210° C.). The reaction mixture is allowed to stand overnight in a sodium hydroxide solution 2 N. The product is extracted with trichloromethane while stirring. The extract is washed with water, dried, filtered and evaporated. The oily residue is purified by column-chromatography over silica gel using a mixture of trichloromethane and methanol (95:5 by volume), saturated with ammonia, as eluent. The pure fractions are collected and the eluent is evaporated. The residue is converted into the hydrochloride salt in 2-propanone and 2-propanol. The salt is filtered off and crystallized from acetonitrile, yielding 4.2 parts of 3-[3-[4-(4-fluorobenzoyl)-1-piperidinyl]propyl]-2-methyl-pyrido[1,2-a]pyrimidin-4(3H)-one dihydrochloride monohydrate; mp. 217.8° C.

What is claimed is:

1. A chemical compound selected from the group consisting of a 3-[(1-piperidinyl)alkyl]-4H-pyrido[1,2-a]pyrimidin-4-one derivative having the formula

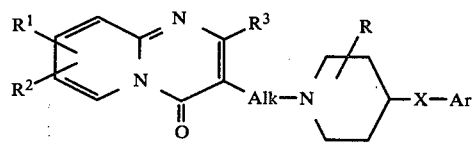

and the pharmaceutically acceptable acid addition salts thereof, wherein $R^1$ and $R^2$ are each independently selected from the groups consisting of hydrogen, lower alkyl, lower alkyloxy, halo and trifluoromethyl;

$R^3$ is a member selected from the group consisting of hydrogen, lower alkyl and aryl;

Alk is a lower alkylene radical;

R is a member selected from the group consisting of hydrogen, lower alkyl, hydroxy, lower alkyloxy and hydroxymethyl in the 2-, 3- or 4-position of the piperidine ring;

X is a member selected from the group consisting of >C=O, >CHOH,

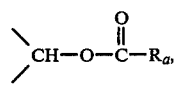

>CH$_2$, >C(O-lower alkyl)$_2$,

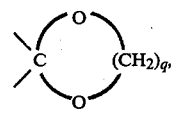

>C=NOH and >C=N-NH$_2$, wherein said $R_a$ is hydrogen or lower alkyl and said q is the integer 2 or 3; and Ar is aryl; wherein said aryl is a member selected from the group consisting of phenyl, substituted phenyl, thienyl, furanyl and pyridinyl, wherein said substituted phenyl has from 1 to 3 substituents each independently selected from the group consisting of halo, lower alkyl, lower alkyloxy, trifluoromethyl, nitro, amino and hydroxy, provided that no more than one substituent is nitro and further provided that said substituents are not simultaneously hydroxy and loweralkyloxy.

2. A chemical compound according to claim 1 wherein R is hydrogen.

3. A chemical compound according to claim 1 wherein R is hydrogen and X is >C=O, >C(O-lower alkyl)$_2$ or

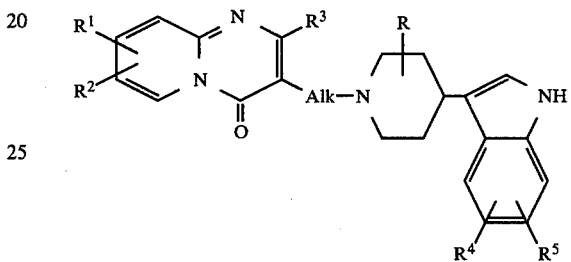

4. A chemical compound according to claim 1 wherein R is hydrogen, X is >C=O and Alk is an 1,2-ethanediyl radical.

5. A chemical compound selected from the group consisting of 3-[2-[4-(4-fluorobenzoyl)-1-piperidinyl]ethyl]-2-methyl-4H-pyrido[1,2-a]pyrimidin-4-one and the pharmaceutically acceptable acid addition salts thereof.

6. A chemical compound selected from the group consisting of a 4H-pyrido[1,2-a]pyrimidin-4-one derivative having the formula and the pharmaceutically acceptable acid addition salts thereof, wherein:

$R^1$ and $R^2$ are each independently selected from the group consisting of hydrogen, lower alkyl, lower alkyloxy, halo and trifluoromethyl;

$R^3$ is a member selected from the group consisting of hydrogen, lower alkyl and aryl;

Alk is a lower alkylene radical;

R is a member selected from the group consisting of hydrogen, lower alkyl, hydroxy, lower alkyloxy, hydroxymethyl in the 2-, 3- or 4-position of the piperidine ring; and $R^4$ and $R^5$ are each independently selected from the group consisting of hydrogen, halo, lower alkyl, lower alkyloxy, trifluoromethyl, nitro, amino and hydroxy;

wherein said aryl is a member selected from the group consisting of phenyl, substituted phenyl, thienyl, furanyl and pyridinyl, wherein said substituted phenyl has from 1 to 3 substituents each independently selected from the group consisting of halo, lower alkyl, lower alkyloxy, trifluoromethyl, nitro, amino and hydroxy, provided that no more than one substituent is nitro and further provided that said substituents are not simultaneously hydroxy and loweralkyloxy.

* * * * *